US012663373B2

(12) United States Patent (10) Patent No.: US 12,663,373 B2
Askenazi et al. (45) Date of Patent: Jun. 23, 2026

(54) DEVICE FOR INSPECTING A HUMAN BODY PORTION AND ASSOCIATED METHOD

(71) Applicant: L'OREAL, Paris (FR)

(72) Inventors: Benjamin Askenazi, Saint-Ouen (FR);
Thierry Wasserman, Clichy (FR);
Emmanuel Malherbe, Clichy (FR);
Thomas Gottschall, Jena (DE)

(73) Assignee: L'OREAL, Paris (FR)

( * ) Notice: Subject to any disclaimer, the term of this patent is extended or adjusted under 35 U.S.C. 154(b) by 113 days.

(21) Appl. No.: 18/711,967

(22) PCT Filed: Nov. 30, 2022

(86) PCT No.: PCT/EP2022/083768
§ 371 (c)(1),
(2) Date: May 21, 2024

(87) PCT Pub. No.: WO2023/099522
PCT Pub. Date: Jun. 8, 2023

(65) Prior Publication Data
US 2025/0020587 A1      Jan. 16, 2025

(30) Foreign Application Priority Data

Dec. 1, 2021    (FR) ........................................ 2112795

(51) Int. Cl.
*G01N 21/55* (2014.01)
*G01N 33/483* (2006.01)
(52) U.S. Cl.
CPC ......... *G01N 21/55* (2013.01); *G01N 33/4833* (2013.01); *G01N 2201/062* (2013.01);
(Continued)
(58) Field of Classification Search
CPC ............... G01N 21/55; G01N 33/4833; G01N 2201/0633
See application file for complete search history.

(56) References Cited

U.S. PATENT DOCUMENTS 5,940,998 A    8/1999  Brauer
9,316,580 B2   4/2016  Landa et al.
(Continued)

FOREIGN PATENT DOCUMENTS

CN      110062932 A  *  7/2019  ......... G06V 40/1324
EP      2284519 B1    12/2015
JP      2014071882 A  *  4/2014  ............. G06V 40/12

OTHER PUBLICATIONS

International Search Report and Written Opinion issued on Feb. 28, 2023 for corresponding PCT Application No. PCT/EP2022/083768.
(Continued)

*Primary Examiner* — Maurice C Smith
(74) *Attorney, Agent, or Firm* — POLSINELLI PC

(57) ABSTRACT

This device for inspecting a human body portion (12) comprises:
a frame (14), defining an observation window (26);
an optical sensor, configured to capture a measurement luminous radiation (C) from the human body portion (12), and
an illumination arrangement, configured to illuminate the human body portion (12), the illumination arrangement comprising at least one light source (30), each light source (30) being configured to produce an emitted luminous radiation (A).
The illumination arrangement comprises at least one concave mirror (32) configured to reflect the emitted luminous radiation (A) produced by at least one of the light sources (30) in a reflected luminous radiation (B), the reflected luminous radiation (B) being collimated toward the observation window (26) so as to illuminate the human body portion (12).

16 Claims, 3 Drawing Sheets

(52) U.S. Cl.
 CPC ................ *G01N 2201/0633* (2013.01); *G01N 2201/0636* (2013.01)

(56) References Cited

U.S. PATENT DOCUMENTS

| | | |
|---|---|---|
| 2006/0023202 A1 | 2/2006 | Delacour |
| 2010/0004719 A1 | 1/2010 | Hamada et al. |
| 2014/0155754 A1 | 6/2014 | Varghese et al. |
| 2019/0104980 A1 | 4/2019 | Farooq et al. |

OTHER PUBLICATIONS

Preliminary Search Report issued on Jun. 29, 2022 for corresponding French Application No. FR 2112795.

* cited by examiner

DEVICE FOR INSPECTING A HUMAN BODY PORTION AND ASSOCIATED METHOD

CROSS REFERENCE TO RELATED APPLICATIONS

This application is a National Phase filing under 35 U.S.C. § 371 of PCT/EP2022/083768, filed on Nov. 30, 2022; which in turn claims benefit of French Application No. 2112795, filed Dec. 1, 2021, both of which are incorporated herein by reference in their entireties.

The present invention relates to a device for inspecting a human body portion comprising:

a frame, defining a window for observing the human body portion, an optical sensor, configured to capture a measurement luminous radiation from the human body portion, and an illumination arrangement, configured to illuminate the human body portion, the illumination arrangement comprising at least one light source, each light source being configured to produce an emitted luminous radiation.

In order to determine the visual properties of a human body portion, and the characteristics associated with such properties, it is customary to use devices for inspecting a human body portion. Such devices are for example intended for inspecting the skin of a human body or hair of a human body.

Such devices generally comprise an illumination arrangement configured to illuminate the human body portion to be inspected. In order to obtain an accurate inspection, it can be advantageous that the illumination arrangement project a collimated luminous radiation, i.e., wherein the rays are substantially parallel with each other, on the human body portion to be inspected.

Known devices then comprise a plurality of light sources, each light source being associated with at least one lens to collimate the light from the light source toward the human body portion to be inspected.

However, such devices are not fully satisfactory. Indeed, incorporating lenses to collimate the light from each light source proves to be costly and cumbersome. Thus, such a device, while enabling an accurate inspection, proves to be costly and cumbersome.

An aim of the invention is then that of obtaining a device for inspecting a human body portion which is accurate, while being less costly and non-cumbersome.

To this end, the invention relates to an inspection device as described above, wherein the illumination arrangement comprises at least one concave mirror, the at least one concave mirror being configured to reflect the emitted luminous radiation produced by at least one of the light sources in a reflected luminous radiation, the reflected luminous radiation being collimated toward the observation window so as to illuminate the human body portion.

The use of a concave mirror configured to reflect the emitted luminous radiation by collimating such a radiation is of particular interest as it provides an illumination enabling an accurate inspection of the human body portion, while helping limit the size and the cost of the collimation device. The reflected luminous radiation thus collimated is particularly suitable for limiting specular glare. Such a luminous radiation furthermore enables good color rendering, which is particularly advantageous in the case where the luminous radiations captured by the sensor are to be processed for example to extract colorimetric data therefrom.

According to further advantageous aspects of the invention, the device for inspecting a human body portion comprises one or more of the following features, taken in isolation or in any technically possible combination:

the at least one concave mirror defines at least one optical convergence region, the or each light source being disposed in the or one of the optical convergence region(s);

the observation window defines a window plane, the reflected luminous radiation passing through the window plane forming an angle between 30° and 60°, preferably between 40° and 50° and more preferably between 42° and 48°, with respect to the window plane;

the frame extends along an observation axis, the optical sensor being disposed on the observation axis, the measurement luminous radiation being parallel with the observation axis;

the device comprises an inspection module configured to inspect the or each light source;

the illumination arrangement comprises between four and twelve light sources;

the device comprises at least two light sources, the frame extending along an observation axis, the observation axis passing through the observation window, each light source being radially at the same non-zero distance from the observation axis;

the device comprises at least four light sources, the orthoradial deviation between two light sources of two pairs of adjacent light sources being greater than the orthoradial deviation of the other pairs of adjacent light sources, the light sources being symmetrical along a plane of symmetry comprising the observation axis;

the at least one concave mirror is the sole concave mirror of the illumination arrangement, the concave mirror being a revolving mirror and being configured to reflect the emitted luminous radiation produced by the or each light source in a reflected luminous radiation;

each light source is a light-emitting diode;

the at least one concave mirror comprises a distal edge, the distal edge being proximally offset from the observation window by a distance between 0 mm and 50 mm; and the device comprises an inner pane housed bearing on the distal edge of the mirror.

The invention furthermore relates to a method for inspecting a human body portion implemented using an inspection device as described above, the method comprising the following steps:

positioning the human body portion facing the observation window of the frame, production of an emitted luminous radiation by the at least one light source;

reflection of the emitted light ray by the at least one concave mirror, the reflected luminous radiation being collimated toward the observation window;

reflection of the reflected light ray by the human body portion, the ray reflected by the human body portion forming a measurement luminous radiation; and capture of the measurement radiation from the human body portion by the optical sensor of the inspection device.

The invention furthermore relates to a method for manufacturing a device for inspecting a human body portion as described above, the manufacturing method comprising the following steps:

providing a modeling of a device for inspecting a non-adapted human body portion, each light source of the modeling being configured to produce a modeling of emitted luminous radiation, the at least one concave mirror of the modeling being configured to reflect the modeling of the emitted luminous radiation in a modeling of reflected luminous radiation, the modeling of reflected luminous radiation being reflected toward the modeling of the observation window without being collimated;

adapting the geometry of the at least one concave mirror of the modeling, such that the modeling of reflected luminous radiation is collimated by the modeling of the concave mirror toward the modeling of the observation window; and manufacturing the device for inspecting a human body portion, said device comprising at least one concave mirror manufactured on the basis of the adapted geometry of the at least one concave mirror of the modeling.

The invention will be easier to understand in view of the following description, provided solely as a non-restrictive example and with reference to the drawings, wherein.

Hereinafter in the description, the term "distal" is used to describe a far position from the user holding the device and the term proximal is used to describe a near position to the user holding the device, a distal element thus being farther from the user holding the device than a proximal element.

Figure 1:
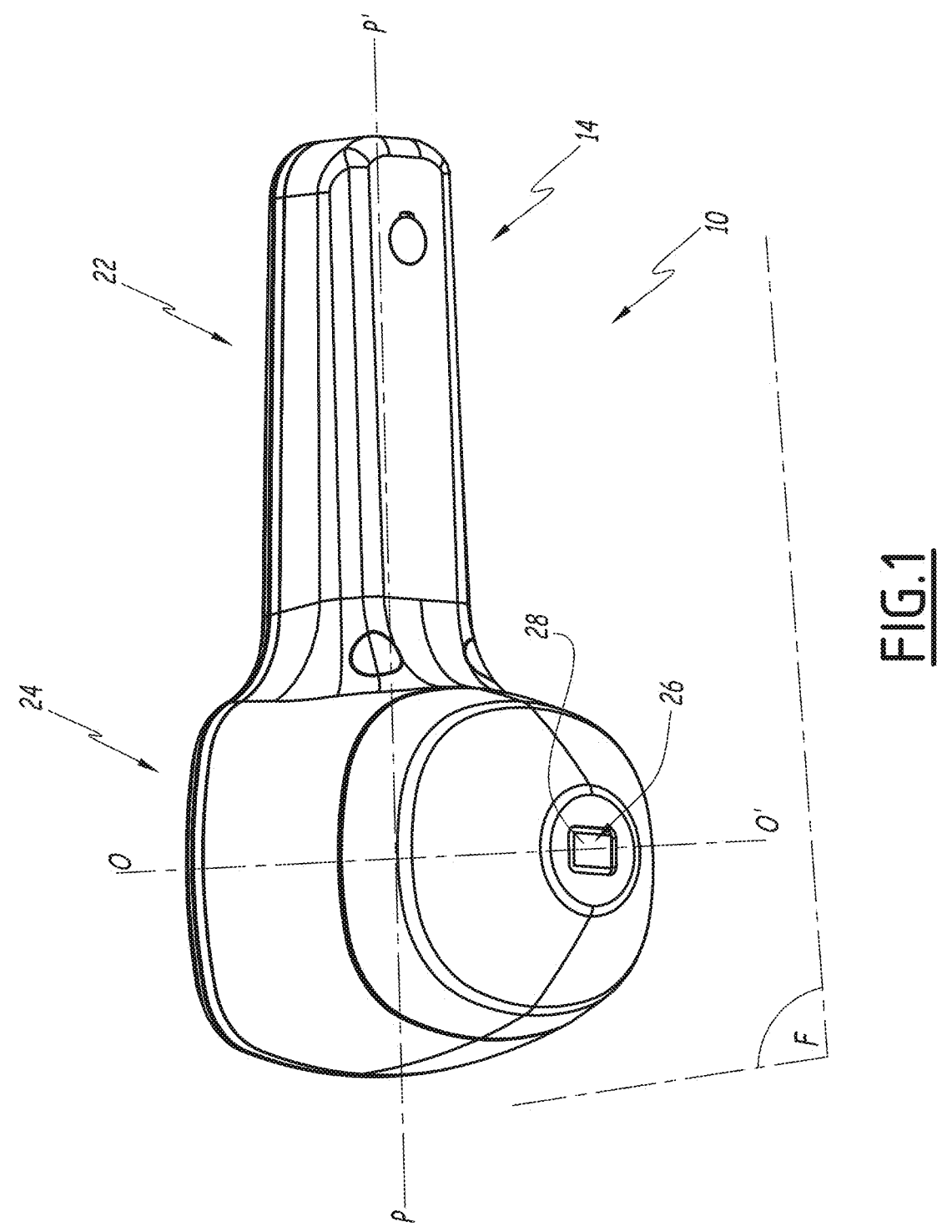
FIG. 1 is a schematic perspective view of a device for inspecting a human body portion.
Figure 2:
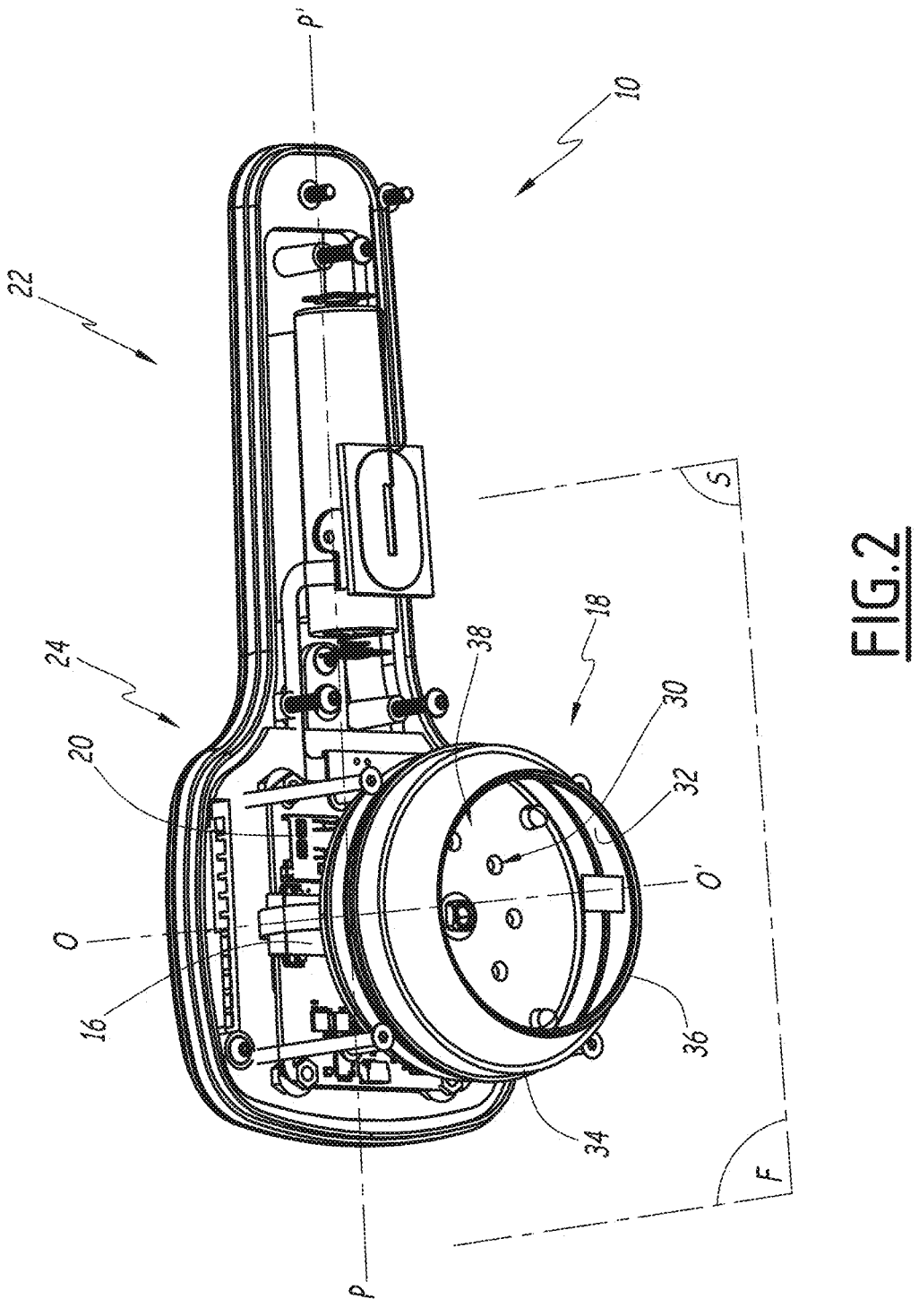
FIG. 2 is a schematic perspective view of the inspection device in FIG. 1, wherein a frame of the device is not shown.

With reference to FIG. 1, a device 10 for inspecting a human body portion 12, comprises a frame 14. As illustrated in FIG. 2, the device further comprises an optical sensor 16, an illumination arrangement 18 and comprises for example a control module 20.

The inspection device 10 Is intended to evaluate the inherent parameters of the human body portion 12.

The human body portion 12 is for example a portion of an individual's skin or a set of an individual's keratin fibers, such as for example a lock of the individual's hair. The inspection device 10 is then for example intended to inspect a lock of hair, and is for example configured to determine the color and/or shine of such a lock of hair.

As seen in FIG. 1, the frame 14 comprises for example a handle 22 and a head 24.

The handle 22 preferably forms a handling for gripping the inspection device 10, the handle then being configured to be held in the hand of a user of the inspection device 10. The handle 22 is for example elongated and defines a gripping axis P-P' of the frame 14.

The head 24 extends from the handle 22. The head 24 is for example intended to be affixed to a human body portion to be inspected. The head 24 is for example elongated and defines an observation axis O-O' of the frame 14. The frame 24 thus extends at least partially along the observation axis O-O'. In the alternative embodiment shown in FIGS. 1 and 2, the observation axis O-O' is substantially perpendicular to the gripping axis P-P'.

The frame 14 defines a window 26 for observing a human body portion. The observation window 26 is for example defined by the head 24 of the frame. The observation window 26 is intended to be disposed facing the human body portion 12 to be inspected.

The observation window 26 is for example disposed along the observation axis O-O', the observation axis O-O' passing through the observation window 26, preferably through the center of the observation window 26.

As seen in FIG. 1, the observation window 26 is for example substantially planar and defines a window plane F.

In the example in FIG. 1, the observation window is rectangular. The observation window is for example elongated along a direction perpendicular to the gripping axis P-P'.

As illustrated in FIG. 1, the frame comprises for example an observation pane 28 housed in the observation window 26.

The optical sensor 16 is configured to capture a measurement luminous radiation C. The optical sensor comprises for example, or is formed by, a camera.

The measurement luminous radiation C is a luminous radiation from the human body portion 12. The measurement radiation C passes for example through the observation window 26 before reaching the optical sensor 16. The measurement radiation C is then for example parallel with the observation axis O-O'.

The optical sensor 16 is then for example disposed on the observation axis O-O'.

The optical sensor 16 is then configured to, based on the measurement radiation C captured, evaluate an inherent parameter of the human body portion 12.

The illumination arrangement 18 is configured to illuminate the human body portion 12, in particular so that the human body portion 12 emits a measurement luminous radiation C, for example by reflecting the light emitted by the illumination arrangement 18.

The illumination arrangement 18 comprises at least one light source 30 and a concave mirror 32.

The illumination arrangement 18 comprises for example between four and twelve light sources 30. In the example in FIG. 2, the illumination arrangement 18 comprises eight light sources 30. In some alternative embodiments, the illumination arrangement 18 comprises more than twelve light sources 30.

When the device 10 comprises at least two light sources 30, each light source is for example disposed radially at the same non-zero distance from the observation axis.

When the device 10 comprises at least two light sources 30, the light sources are for example symmetrical along at least one plane of symmetry S.

The at least one plane of symmetry S comprises for example the observation axis O-O'.

When the device 10 comprises at least four light sources, the orthoradial deviation between two light sources 30 of two pairs of adjacent light sources 30 is greater than the orthoradial deviation of the other pairs of adjacent light sources 30 (not shown). At least one plane of symmetry S then extends for example between the two light sources 30 of the two pairs of adjacent light sources 30, wherein the orthoradial deviation is greater than the orthoradial deviation of the other pairs of adjacent light sources 30.

The light sources are then thus split into two separate light source groups, for example disposed on either side of the plane of symmetry S.

For example, in an alternative embodiment wherein the device comprises at least six light sources, the orthoradial deviation between two light sources of two pairs of adjacent light sources 30 is for example equal to 90° whereas the orthoradial deviation between the other pairs of adjacent light sources is for example equal to 45°. One of the planes of symmetry S then extends for example between the two light sources 30 of the two pairs of adjacent light sources 30, wherein the orthoradial deviation is greater than the ortho-radial deviation of the other pairs of adjacent light sources 30.

Each light source 30 is configured to produce an emitted luminous radiation A.

The emitted luminous radiation A produced by the or each light source 30 diverges from said at least one light source 30. In other words, the rays emitted by each light source 30 are not collimated and diverge from the light source 30 from which they were emitted.

Each light source 30 is for example a light-emitting diode, also known as LED. In particular, each light source 30 is for example a white diode and more specifically a diode with a high color rendering index.

The color rendering index of the light sources 30 is for example greater than 90.

In a specific embodiment (not shown), at least one of the light sources 30 comprises a light-emitting diode as described above and additionally comprises a converging lens. The converging lens then reduces in this alternative embodiment the divergence of the luminous radiation emitted by the light-emitting diode, the emitted light ray A produced by such a light source 30 thus being less divergent than the light ray that would have been emitted by a light-emitting diode alone.

The control module 20 is configured to control the or each light source 30. The control module 20 is for example connected to an electric power supply (not shown) and is configured to switch the at least one light source 30 between an on state, wherein the light source 30 emits an emitted luminous radiation A, and an off state wherein the light source does not emit an emitted luminous radiation A.

The control module 20 is for example, additionally, configured to control the intensity of the emitted luminous radiation A produced by the at least one light source 30 and/or the color, or in other words the wavelength, the emitted luminous radiation A produced by the at least one light source 30.

The control module 20 is for example configured to control the polarization of the emitted luminous radiation A produced by the least one light source 30.

The control module 20 is moreover configured to control the general direction of the emitted luminous radiation A produced by the least one light source 30.

The device 10 comprises for example a controlling member (not shown) forming a human-machine interface, the controlling member being configured to control the control member.

When the device 10 comprises at least two light sources 30, the control module 20 is configured to control each light source 30 independently from one another.

The concave mirror 32 is configured to reflect the emitted luminous radiation A produced by the at least one of the light sources 10 in a reflected radiation B.

Concave means that the mirror is hollow on the reflective face thereof, i.e., a line tangent to the mirror extends from the side of mirror opposite the reflective face of the mirror. Thus, concave mirror 32 does not only denote a mirror of constant concavity, the concavity of the concave mirror 32 being for example variable.

The concave mirror 32 preferably defines at least one optical convergence region. In particular, the optical convergence region corresponds to a collimated light ray convergence region if the collimated light rays are emitted from the observation window 26 to the concave mirror 32. The at least one optical convergence region is then comparable to an optical focal point of the concave mirror 32 and can as such be described as a pseudo optical focal point.

The or each light source 30 is then disposed in the or one of the optical focal point(s), such that the emitted luminous radiation A produced by the light source 30 reflected by the concave mirror 32 is reflected in a reflected luminous radiation B collimated toward the observation window 26.

Figure 3:
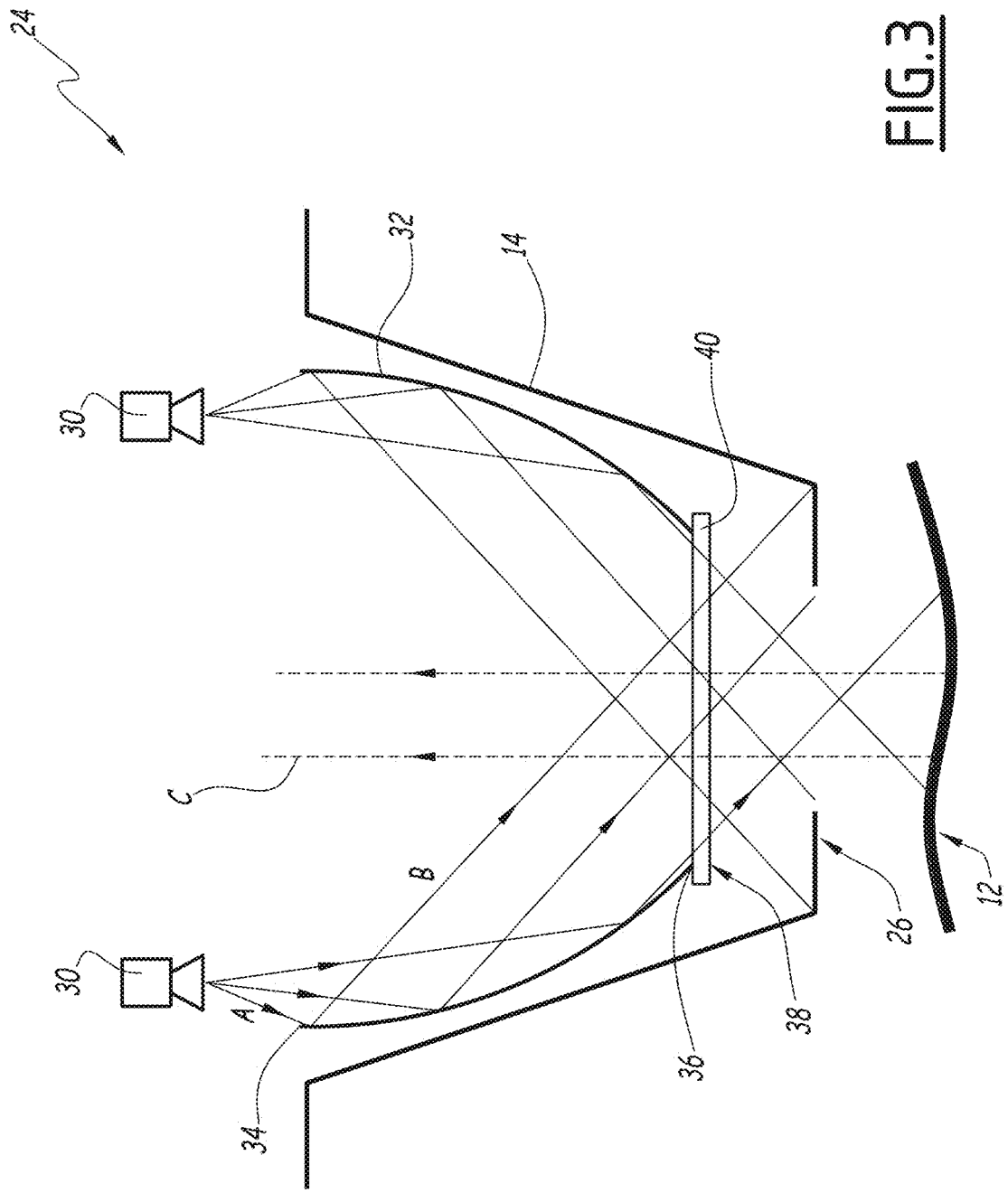
FIG. 3 is a block diagram of the inspection device in FIGS. 1 and 2.

The concave mirror 32 is then comparable to a pseudo-parabolic mirror. The concave mirror 32 is for example formed by a revolving pseudo-parabolic mirror or by a portion of a revolving pseudo-parabolic mirror. Pseudo-parabolic means here that the general shape of the concave mirror 32 in a sectional view along a plane passing through the observation axis O-O', as illustrated in FIG. 3, has a similar shape to a parabola, i.e., a curve defined by a second-degree polynomial function. However, as seen in FIG. 3, and for each given angular segment about the axis O-O', the concave mirror 32 defines a different optical focal point, said optical focal points defining the optical convergence region together. As such, the concave mirror, even though it is comparable to a parabolic mirror, is generally not strictly parabolic.

The geometry of the concave mirror 32 is for example obtained following digital simulations. The geometry of the concave mirror is for example obtained following an iterative digital simulation accounting for the relative position of the at least one light source 30, the concave mirror 32 and the observation window 26, the observation window making it possible to determine the position of the human body portion 12.

During the iterative digital simulation aimed at obtaining the geometry of the concave mirror 32, the geometry of a modeling of the concave mirror is iteratively modified until the emitted luminous radiations from a modeling of the at least one light source 30 pass through a modeling of the observation window while being collimated so as to illuminate a modeling of the human body portion 12. In other words, the geometry of the modeling of the concave mirror is iteratively modified until the geometry of the concave mirror 32 enables the collimation of the light rays through the observation window so as to illuminate the human body portion 12 using collimated light rays.

During the iterative digital simulation, the concavity of the concave mirror 32 is more specifically calculated so that the concave mirror 32 enables the collimation of the light rays through the observation mirror 26. In specific alternative embodiments not illustrated, the mirror 32 comprises for example locally a convex region, the term concave thus to be understood as generally concave.

The emitted luminous radiation A, diverging from a given light source 30 is collimated by the concave mirror 32 by forming the reflected luminous radiation B.

Collimated means that the rays forming the reflected luminous radiation B extend substantially parallel with one another to the observation window 26. It is thus understood that the angle formed between any two rays of the collimated reflected radiation B is less than 5° and preferably less than 2°. It will be understood here that only the portion of the emitted radiation A reflected by the concave mirror 32, and forming the reflected luminous radiation B, is collimated.

The length of the reflected luminous radiation B, i.e., the length of the luminous radiation extending between the concave mirror 32 and the human body portion 12, is preferably between 20 mm and 60 mm, more preferably between 30 and 40 mm. In other words, the vertical distance, i.e., along the observation axis O-O', between the point where the emitted light ray A is reflected in the reflected radiation B, and the human body portion 12, is between 15 mm and 45 mm, and preferably between 20 mm and 35 mm.

The reflected luminous radiation B is collimated toward the observation window 26 so as to illuminate the human body portion 12, when the human body portion 12 is disposed facing the observation window 26. The reflected luminous radiation B is in particular intended to pass through the observation window 26. The reflected luminous radiation B thus collimated is for example intended to be reflected by the human body portion 12, the luminous radiation thus reflected by the human body portion 12 forming for example the measurement radiation C.

The reflected luminous radiation B passes for example through the window plane F forming an angle between 30° and 60°, preferably between 40° and 50° and more preferably between 42° and 48°, with respect to the window plane F. In the example in FIG. 3, the reflected luminous radiation B passes through the window plane F forming an angle of 45° with respect to the window plane F.

The measurement radiation C passes for example through the window plane F forming an angle between 85° and 95° with respect to the window plane F, and preferably forming an angle equal to 90° with respect to the window plane.

Thus, as seen in FIG. 3, the human body portion 12 is illuminated by means of the reflected luminous radiation B passing through the observation window 26 being inclined with respect to the window plane F, the optical sensor 16 capturing the measurement radiation C plumb with the human body portion 12.

The illumination arrangement 18 preferably comprises a single concave mirror 32, as illustrated in FIG. 2. The single concave mirror 32 is then configured to reflect the emitted light radiation A, produced by the or each light source 30, in a reflected luminous radiation B.

In an alternative embodiment not shown, the illumination arrangement 18 comprises a plurality of concave mirrors 32. Each concave mirror 32 is for example disposed facing a light source 30 so as to reflect the emitted luminous radiation A produced by said light source in a reflected luminous radiation B. As seen above, the geometry of these concave mirrors 32 is calculated so that the concave mirror 32 enables the collimation of the light rays through the observation window 26. Such concave mirrors 32 are for example independent from one another. Alternatively, the concave mirrors 32 are connected to each other by a connection mirror (not illustrated). The concave mirrors are then comparable to concave regions of a mirror formed by said concave mirror and by the connection mirror, the geometry of such a mirror being, as seen above, adapted to enable the collimation of the reflected luminous radiation B through the observation window 26.

In the embodiment in FIG. 2, the concave mirror 32 is a revolving mirror about the observation axis O-O'.

The or each mirror 32 comprises at least one proximal edge 34 and at least one distal edge 36. The proximal edge 34 is radially wider than the distal edge 36.

The distal edge 36 extends for example in a plane, for example in a plane substantially parallel with the observation window 26. When the concave mirror 32 is a revolving mirror about the observation axis O-O', the distal edge 36 is for example circular in a plane substantially parallel with the observation window 26. When the illumination arrangement 18 comprises a plurality of concave mirrors 32, the distal edge 36 of each mirror 32 is for example a circle portion extending in a plane substantially parallel with the observation window 26.

The distal edge 36 is preferably proximally offset from the observation window 26 by a distance between 0 mm and 50 mm and preferably between 10 and 30 mm, the distance being preferably measured perpendicularly to the plane formed by the observation window 26. In other words, the observation window 26 is offset along the observation axis O-O', toward the human body portion 12, by a distance between 5 mm and 50 mm and preferably between 10 and 30 mm.

In an alternative embodiment illustrated in FIG. 3, the device 10 comprises an inner pane 40. The inner pane 40 is housed bearing on the distal edge 36 of the mirror 32, the inner pane 40 then extending for example substantially in the plane formed by the distal edge 36.

A method for inspecting a human body portion 12 implemented using an inspection device 10 as described above will now be described.

A human body portion is first of all presented facing the observation window 26 of the frame 14. For example, a lock of hair is presented facing said observation window 26. The human body portion 12 is then preferably aligned on the observation axis O-O'.

The emitted luminous radiation A is then produced by the at least one light source 30. Each source 30 produces for example an emitted luminous radiation.

The emitted luminous radiation A is then reflected by the concave mirror 32. The reflected light ray B thus obtained by the reflection of the emitted light ray A on the concave mirror 32 is collimated toward the observation window 26. In other words, the reflection of the emitted luminous radiation A on the concave mirror 32 collimates said emitted light ray A in a reflected luminous radiation B toward the observation window 26.

The reflected radiation B is then reflected by the human body portion 12. The radiation from the reflection of the reflected radiation B on the human body portion 12 forms a measurement luminous radiation C, the measurement luminous radiation C making it possible to characterize the human body portion 12.

The measurement radiation C from the human body portion is then captured by the optical sensor 16. The optical sensor 16 and/or a processing module (not shown) are then configured to determine the visual properties of the human body portion 12 using the measurement radiation C, and determine the characteristics associated with such properties.

A method for manufacturing a device 10 for inspecting a human body portion 12 as described above will now be described.

The manufacturing method comprises a step of providing a modeling of a device for inspecting a non-adapted human body portion 12, followed by a step of adapting the modeling and more specifically the modeling of the concave mirror 32, followed by a step of manufacturing the device based on the adapted modeling.

During the provision step, the modeling of the device 10 for inspecting a non-adapted human body portion 12 is provided. Each light source 30 of the modeling is configured to produce a modeling of emitted luminous radiation A. The at least one concave mirror 32 of the modeling is configured to reflect the modeling of the emitted luminous radiation A in a modeling of reflected luminous radiation B. The modeling of reflected luminous radiation is reflected toward the modeling of the observation window 26 without being collimated. In other words, the modeling of the device 10 for inspecting a human body portion 12 is not adapted in that the geometry of the at least one concave mirror 32 of the modeling does not make it possible to obtain a collimated modeling of reflected luminous radiation B.

During the adaptation step, the geometry of the at least one concave mirror 32 of the modeling is adapted such that the modeling of the reflected luminous radiation B is collimated by the modeling of the concave mirror 32 toward the modeling of the observation window 26. The adaptation step comprises for example an iterative calculation of a modified geometry of the at least one concave mirror 32 of the modeling, a new modified geometry of the at least one concave mirror 32 being calculated until an adapted concave mirror 32 geometry is obtained such that the reflected luminous radiation B is collimated.

During the manufacturing step, the device 10 for inspecting a human body portion is manufactured based on the adapted geometry of the modeling of said device 10 and more specifically based on the adapted geometry of the at least one concave mirror 32 of the modeling. In particular, the concavity of the concave mirror 32 corresponds to the concavity of the modeling of the adapted concave mirror 32.

The inclination of the reflected radiation B with respect to the observation window plane F is of particular interest for improving the lighting of the human body portion 12, such a lighting limiting for example undesirable glare on the human body portion 12.

The use of a control module is particularly advantageous for adapting the use of the inspection device to different contexts of use.

The use of a number of light sources 30 between four and twelve light sources enables lighting by collimated emitted light rays A from several different orientations, which helps improve the precision of the device.

The specific orthoradial positioning of the light sources as described above furthermore makes it possible to obtain a lighting particularly adapted to elongated objects such as locks of hair, by limiting the specular reflection associated with such elongated objects.

The use of a single concave mirror enables a particularly simple set-up and a particularly economical design of the inspection device 10.

The use of light-emitting diodes is furthermore particularly relevant for limiting the manufacturing cost while having a light source 30 in which the properties of the emitted luminous radiation A are adapted to the use thereof in an inspection device 10.

A person skilled in the art will understand that the embodiments and alternative embodiments described hereinabove can be combined to form new embodiments, provided that they are technically compatible.

The invention claimed is:

1. An inspection device for inspecting a human body portion, comprising:
   a frame, defining a window for observing the human body portion;
   an optical sensor, configured to capture a measurement luminous radiation (C) from the human body portion, and
   an illumination arrangement, configured to illuminate the human body portion, the illumination arrangement comprising at least one light source, each light source being configured to produce an emitted luminous radiation (A),
   wherein the illumination arrangement comprises at least one concave mirror, the at least one concave mirror being configured to reflect the emitted luminous radiation (A) produced by at least one of the light sources in a reflected luminous radiation (B), the reflected luminous radiation (B) being collimated toward the observation window so as to illuminate the human body portion,
   wherein the frame extends along an observation axis (O-O'), the optical sensor being disposed on the observation axis (O-O'), the measurement luminous radiation (C) being parallel with the observation axis.

2. The inspection device according to claim 1, wherein the at least one concave mirror defines at least one optical convergence region, the or each light source being disposed in the or one of the optical convergence region(s).

3. The inspection device according to claim 1, wherein the observation window defines a window plane (F), the reflected luminous radiation (B) passing through the window plane (F) forming an angle between 30° and 60° with respect to the window plane (F).

4. The inspection device according to claim 1, wherein the device comprises a control module configured to control the or each light source.

5. The inspection device according to claim 1, wherein the illumination arrangement comprises between four and twelve light sources.

6. The inspection device according to claim 1, wherein the device comprises at least two light sources, the frame extending along an observation axis (O-O'), the observation axis (O-O') passing through the observation window, each light source being radially at the same non-zero distance from the observation axis (O-O').

7. The inspection device according to claim 6, wherein the device comprises at least four light sources, the orthoradial deviation between two light sources of two pairs of adjacent light sources being greater than the orthoradial deviation of the other pairs of adjacent light source, the light sources being symmetrical along a plane of symmetry(S) comprising the observation axis (O-O').

8. The inspection device according to claim 1, wherein the at least one concave mirror is the sole concave mirror of the illumination arrangement, the concave mirror being configured to reflect the emitted luminous radiation (A) produced by the or each light source in a reflected luminous radiation (B).

9. The inspection device according to claim 1, wherein each light source is a light-emitting diode.

10. The inspection device according to claim 1, wherein the at least one concave mirror comprises a distal edge, the distal edge being proximally offset from the observation window by a distance between 0 mm and 50 mm.

11. The inspection device according to claim 10, wherein the device comprises an inner pane housed bearing on the distal edge of the mirror.

12. A method for inspecting a human body portion implemented using an inspection device according to claim 1, the method comprising the following steps:
   positioning the human body portion facing the observation window of the frame,
   production of an emitted luminous radiation (A) by the at least one light source;
   reflection of the emitted light ray (A) by the at least one concave mirror, the reflected luminous radiation (B) being collimated toward the observation window;
   reflection of the reflected light ray (B) by the human body portion, the ray reflected by the human body portion forming a measurement luminous radiation (C); and
   capture of the measurement radiation (C) from the human body portion by the optical sensor of the inspection device.

13. A method for manufacturing a device for inspecting a human body portion according to claim 1, the manufacturing method comprising the following steps:

proviiding a modeling of a device for inspecting a non-adapted human body portion, each light source of the modeling being configured to produce a modeling of emitted luminous radiation (A), the at least one concave mirror of the modeling being configured to reflect the modeling of the emitted luminous radiation (A) in a modeling of reflected luminous radiation (B), the modeling of reflected luminous radiation being reflected toward the modeling of the observation window without being collimated;

adapting the geometry of the at least one concave mirror of the modeling, such that the modeling of reflected luminous radiation (B) is collimated by the modeling of the concave mirror toward the modeling of the observation window; and manufacturing the device for inspecting a human body portion, said device comprising at least one concave mirror manufactured on the basis of the adapted geometry of the at least one concave mirror of the modeling.

14. The inspection device according to claim 2, wherein the observation window defines a window plane (F), the reflected luminous radiation (B) passing through the window plane (F) forming an angle between 30° and 60° with respect to the window plane (F).

15. The inspection device according to claim 2, wherein the device comprises a control module configured to control the or each light source.

16. The inspection device according to claim 3, wherein the device comprises a control module configured to control the or each light source.

* * * * *